United States Patent
Williams et al.

(10) Patent No.: US 6,528,791 B1
(45) Date of Patent: Mar. 4, 2003

(54) INFRARED SPECTROPHOTOMETER EMPLOYING SWEEP DIFFRACTION GRATING

(75) Inventors: Kevin G. Williams, Pinole, CA (US); Joseph John Kurtz, El Cerrito, CA (US)

(73) Assignee: Andros Incorporated, Richmond, CA (US)

( * ) Notice: Subject to any disclaimer, the term of this patent is extended or adjusted under 35 U.S.C. 154(b) by 0 days.

(21) Appl. No.: 09/688,054

(22) Filed: Oct. 13, 2000

(51) Int. Cl.$^7$ .................................................. G01J 3/06
(52) U.S. Cl. ............................. 250/339.13; 250/339.08
(58) Field of Search .................... 250/339.13, 339.08, 250/339.11, 338.1, 338.5, 343, 458.1; 356/39, 318, 301, 328, 334, 437, 454; 600/322

(56) References Cited

U.S. PATENT DOCUMENTS

| | | | |
|---|---|---|---|
| 3,711,708 A | * 1/1973 | Dolin et al. ........... 250/339.13 |
| 3,953,734 A | 4/1976 | Dimeff | |
| 4,013,260 A | 3/1977 | McClatchie | |
| 4,216,439 A | 8/1980 | Pond et al. | |
| 4,290,696 A | 9/1981 | Mould et al. | |
| 4,346,296 A | 8/1982 | Passaro | |
| 4,708,477 A | 11/1987 | Kenji et al. | |
| 4,914,719 A | * 4/1990 | Conlon et al. ............... 250/339 |
| 5,206,701 A | 4/1993 | Taylor et al. | |
| 5,223,715 A | * 6/1993 | Taylor ........................ 250/343 |
| 5,231,462 A | * 7/1993 | Dschen ........................ 356/328 |
| 5,450,193 A | * 9/1995 | Carlsen et al. ............... 356/301 |
| 5,479,258 A | 12/1995 | Hinnrichs et al. | |
| 5,621,744 A | 4/1997 | Kikuchi et al. | |
| 6,006,119 A | * 12/1999 | Soller et al. ................. 600/322 |
| 6,118,577 A | 9/2000 | Sweatt et al. | |
| 6,236,456 B1 | * 5/2001 | Giebeler et al. ............. 356/318 |
| 6,304,767 B1 | * 10/2001 | Soller et al. ................. 600/322 |

OTHER PUBLICATIONS

Dexter Research Center, Inc. *Model DR46 Dual Element Thermopile Detector.*

* cited by examiner

Primary Examiner—Constantine Hannaher
Assistant Examiner—Otilia Gabor
(74) Attorney, Agent, or Firm—Coudert Brothers LLP

(57) ABSTRACT

Very generally, the gas analyzer of the invention includes a source of infrared energy, a sample cell for containing an analyte gas mixture positioned in the path of infrared energy, and a monochrometer including a movable diffraction grating for producing a beam of infrared energy wherein the constituent wavelengths are spetrally separated. The device also includes a wide band interference filter for transmitting a predetermined wavelength band spanning the characteristic absorption wavelength of each of a plurality of constituent gases in the analyte gas mixture. A detector positioned to receive radiation passing through the filter produces an electrical response related to the infrared energy impinging thereon. The monochrometer includes provision for moving the diffraction grating to sequentially cause infrared energy of different wavelengths to impinge upon the detector, and for intermittently causing infrared energy directed toward the detector from the source to be blocked by the interference filter.

4 Claims, 1 Drawing Sheet

INFRARED SPECTROPHOTOMETER EMPLOYING SWEEP DIFFRACTION GRATING

FIELD OF THE INVENTION

This invention relates to infrared gas analyzers and, more particularly, to an improved infrared gas analyzer capable of high accuracy and fast response, yet still relatively low in cost.

BACKGROUND OF THE INVENTION

Many types of infrared gas analyzers utilize an infrared source to produce and direct infrared energy through an unknown gas mixture contained in a sample cell. The energy passing through the sample cell is detected and electrical signals are produced representative thereof. These signals are processed to produce an output indicating the concentration of one or more of the constituents of the gas mixture in the sample cell.

Such gas analyzers utilize the principle that various gases exhibit a substantial absorption characteristic at specific wavelengths in the infrared radiation spectrum. A gas analyzer of this type is shown and described in U.S. Pat. No. 4,013,260, McClatchie, et al. issued Mar. 22, 1977, and assigned to the assignee of the present invention. Another type of infrared gas analyzer is shown and described in U.S. Pat. No. 3,953,734, Dimeff, issued Apr. 27, 1976, and assigned to the United States of America.

In both of the above cited patents, and in similar types of infrared gas analyzers, the wavelength band of the beam of infrared energy passing through the sample cell containing the unknown gas mixture is changed periodically by the interposition of one or more filters in the path of the light beam. Typically, each filter passes only radiation at a characteristic absorption wavelength band of a particular gas of interest. Another filter may also be used as a reference filter at a wavelength band close to but not substantially overlapping the characteristic absorption wavelength band of any of the gases present in the sample cell.

Gas analyzers of the foregoing described type usually continuously reference the radiation detected at the characteristic bands to radiation detected at reference levels (i.e., a non-absorbed wavelength and a dark or totally blocked level). By doing so, the effect of so-called drift is minimized, and the effect of background noise is reduced. Drift can occur as a result of contamination on the windows in the sample cell which will attenuate the radiation passing therethrough and which could be interpreted erroneously as indicating the presence of the gas to be detected in the gas sample. Drift can also be caused by shifts in the output of the detector, inherent in many detector constructions, and temperature changes in the source of the infrared radiation. The process of correcting for drift is sometimes referred to as span stabilization.

One such analyzer is described in Passaro, et al., U.S. Pat. No. 4,346,296. In this disclosure, an infrared source emits infrared radiation at relatively constant intensity over a relatively broad spectrum. The infrared radiation from the source is interrupted periodically by a chopper wheel. After passing through the sample cell, the chopped infrared radiation is detected by respective detectors. In each case the radiation is filtered by a narrow passband filter so that each detector is effectively sensitive only to the radiation of a particular narrow band of frequencies corresponding to a respective absorption frequency characteristic of one of the respective gases. The respective detection signals are thus systematically related to the concentration of each of the respective gases. Because of the chopper wheel, these signals are AC signals at the chopper wheel frequency. The signals are then amplified, detected and filtered to produce corresponding DC signals.

Gas analyzers that employ multiple filters, rotating filter wheels, and/or chopper wheels or the like require a number of relatively expensive components, are subject to failure as a consequence of rapidly rotating parts, and are relatively large in size. It is desirable to provide a gas analyzer design in which size, failure likelihood, and rapidly rotating parts are reduced or eliminated.

Accordingly, it is an object of the present invention to provide an improved infrared spectrophotometer for analyzing gases.

Another object of the invention is to provide an improved gas analyzer which is relatively low in cost.

Another object of the invention is to provide an improved gas analyzer which is relatively smaller in size.

These and other objects of the invention will be understood more particularly from the following description taken in connection with the accompanying drawings wherein:

SUMMARY OF THE INVENTION

Figure 1:
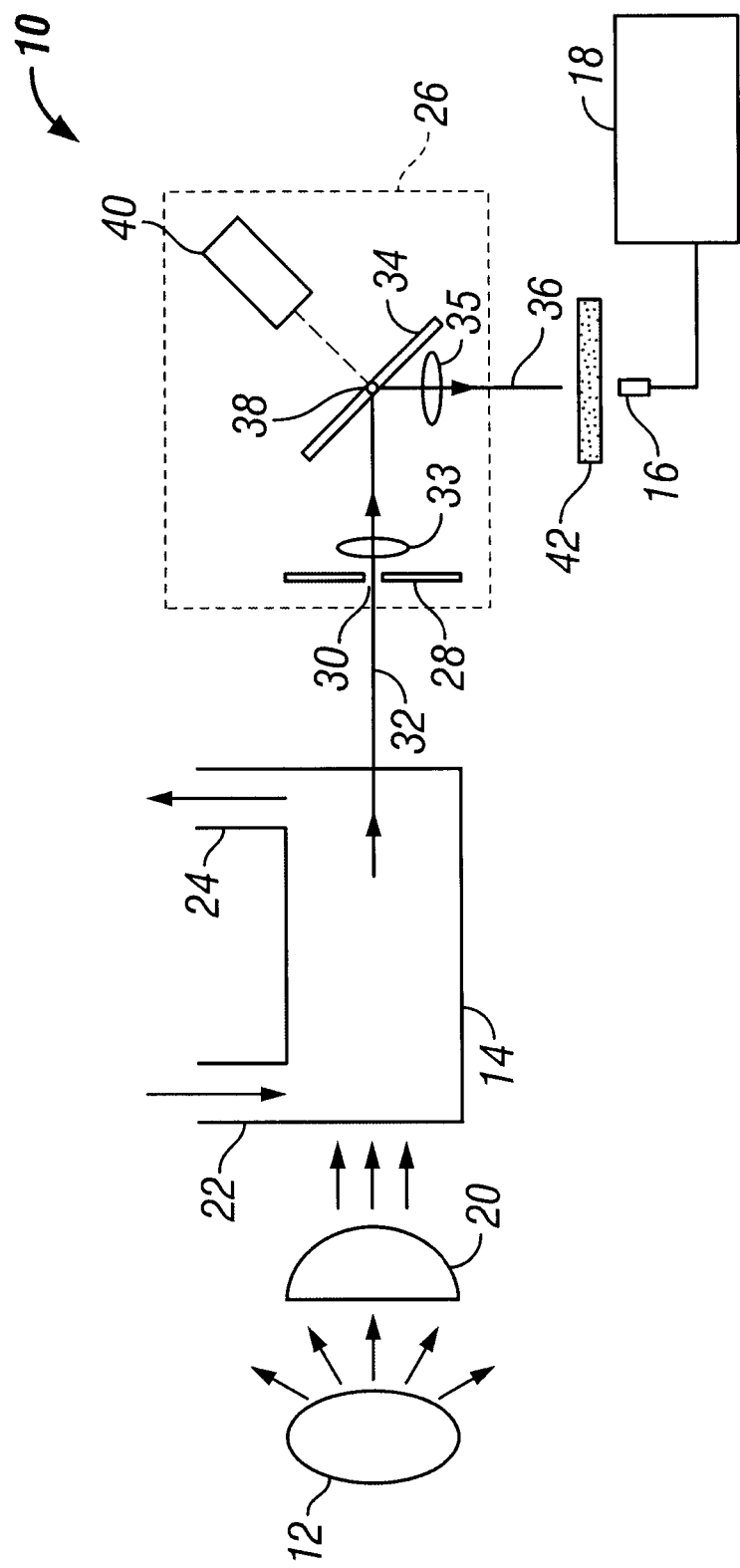
FIG. 1 is a schematic diagram of a gas analyzer constructed in accordance with the invention.

Very generally, the gas analyzer of the invention includes a source of infrared energy, a sample cell for containing an analyte gas mixture positioned in the path of infrared energy, and a monochromator including a movable diffraction grating for producing a beam of infrared energy wherein the constituent wavelengths are spectrally separated. The device also includes a wide band interference filter for transmitting a predetermined wavelength band spanning the mixture. A detector positioned to receive radiation passing through the filter produces an electrical response related to the infrared energy impinging thereon. The monochromator includes provision for moving the diffraction grating to sequentially cause infrared energy of different wavelengths to impinge upon the detector, and for intermittently causing infrared energy directed toward the detector from the source to be blocked by the interference filter.

DETAILED DESCRIPTION OF THE INVENTION

Referring now to FIG. 1, there is shown a dispersive gas analyzer 10 including a source 12 of infrared energy, a sample cell 14, a detector 16, and a signal processor 18. The sample cell 14 contains a gas mixture to be analyzed. The gas mixture includes one or more gases of interest in the mixture Each of the gases has an absorption characteristic associated therewith, as hereinbelow described. The infrared energy produced by the source 12 is collimated by a lens 20 before passing through the sample cell 14. As the infrared energy passes through cell 14, the gas mixture absorbs a portion of such energy. The gas mixture to be analyzed enters the sample cell 14 through an inlet port 22 and leaves the sample cell 14 via an exit port 24.

Prior art analyzers, as mentioned above, typically employ some type of means for modulating and separating the infrared energy, either before it passes through the sample cell or after it leaves the sample cell. Such analyzers have typically included choppers, rotating filter wheels, and the like in order to provide the beam modulation and wavelength separation. In the gas analyzer of the present invention, a monochromator is employed, indicated generally at 26. The monochromator contains an entrance mask 28 defining a slit 30, through which infrared energy indicated by the line 32 passes. A diffraction grating mirror 34 is positioned in the path of infrared energy entering the monochromator 26, through the slit 30, and radiation is passed thereto by a collimating lens or mirror 33. The diffraction grating mirror 34 may be of any suitable construction, such as a highly reflective planar mirror upon the reflecting surface of which has been photolithographed a diffraction grating pattern. The result is that the beam 32 of infrared energy is reflected and the beam is separated into its constituent wavelength spectra.

The resultant beam is shown passing via a focusing lens or mirror 35 and exiting the monochromator 26 at 36. Typical monochromators are provided with an exit mask defining an exit slit. In the preferred embodiment of the present invention, however, such an exit slit is not employed for the reasons set forth below.

The grating mirror 34 is mounted on a pivot 38 and is mechanically coupled to a motor 40 which can rotate the mirror 34 on the pivot 38. Suitable synchronizing structure, not shown, for determining the position of the mirror is provided so that the mirror movement can be synchronized with the signal processor. When movement of the diffraction grating is referred to herein, such phrase is intended to include any system in which the diffraction pattern is swept across the detector.

The beam 36 exiting the monochromator 26 passes through a wide band interference filter 42. The interference filter 42 is selected to have a pass band which includes the infrared absorption bands of gases of interest-to be analyzed, but which blocks wavelengths outside those within the bandwidth of interest.

The size of the detector 16, which may be a lead selenide detector constructed in accordance with known prior art principles, is selected to be a width corresponding to a narrow wavelength band of the energy reflected by the diffraction mirror 34. That is, the radiation responsive area of the cell 16 facing the wide band interference filter 42 corresponds to a narrow bandwidth within the total energy reflected by the mirror 34. This obviates the need for an exit slit in the monochromator 26.

As the position of the diffraction grating mirror 34 is varied by the motor 40, the wavelength of the light beam 36 seen by the detector 16 will change. Thus, the detector 16 is capable of looking at a series of wavelength bands within the light passing through the sample cell 14. At wavelength bands corresponding to the absorption wavelength characteristic of a particular gas of interest, the output of the detector will inversely correspond to the amount of absorption of infrared energy at that wavelength. The angles of the grating are selected so that the detector sees a bandwidth which corresponds to a gas of interest. This information is passed to the processing circuit 18 to be suitably processed in accordance with well-known signal processing principles utilized in gas analyzers. Accordingly, the need for a series of separate narrow band filters is obviated.

The grating 34 is so mounted and oriented that the motor 40 may position the mirror to periodically direct energy at the detector 16 which is beyond the pass band of the interference filter 42. When this occurs, no infrared energy passing through the sample cell 14 will be seen by the detector 16. By periodically interrupting the infrared energy in this way, the need for a chopper wheel or similar type of shutter to produce a span stabilization signal is obviated.

The advantages of the gas analyzer construction described above will become readily apparent to those skilled in the art. The analyzer may be lower in cost, more compact and more reliable of operation. Various modifications of the invention in addition to those shown and described above will become apparent to those skilled in the art and are intended to fall within the scope of the appended claims.

What is claimed is:

1. A gas analyzer comprising a source of infrared energy, a sample cell for containing an analyte gas mixture positioned in the path of infrared energy, a monochromator including a movable diffraction grating for producing a beam of infrared energy wherein the constituent wavelengths are separated spectrally, a wide band interference filter for transmitting a predetermined wavelength band spanning the characteristic absorption wavelength of each of a plurality of constituent gases in the analyte gas mixture, a detector positioned to receive radiation passing through said filter to produce an electrical response related to the infrared energy impinging thereon, said monochromator including provision for moving said diffraction grating to sequentially cause infrared energy of different wavelengths to impinge upon said detector and for intermittently causing infrared energy that would otherwise reach said detector from said source to be blocked by said interference filter, and thereby facilitating span stability.

2. An infrared gas analyzer according to claim 1 wherein said diffraction grating comprises a diffraction grating mirror.

3. A gas analyzer according to claim 1 wherein the area of said detector which is responsive to infrared energy is selected to correspond with a predetermined bandwidth.

4. A gas analyzer comprising a source of infrared energy, a sample cell for containing an analyte gas mixture positioned in the path of infrared energy, a monochromator including a movable diffraction grating for producing a beam of unmodulated infrared energy wherein the constituent wavelengths are separated spectrally, a wide band interference filter for transmitting a predetermined wavelength band spanning the characteristic absorption wavelength of each of a plurality of constituent gases in the analyte gas mixture, a detector positioned to receive radiation passing through said filter to produce an electrical response related to the infrared energy impinging thereon, said monochromator including provision for moving said diffraction grating to sequentially cause infrared energy of different wavelengths to impinge upon said detector and for intermittently causing infrared energy directed toward said detector from said source to be blocked by said interference filter.

* * * * *